United States Patent [19]

Edrich et al.

[11] Patent Number: 6,066,084

[45] Date of Patent: May 23, 2000

[54] METHOD AND APPARATUS FOR FOCUSED NEUROMAGNETIC STIMULATION AND DETECTION

[75] Inventors: Jochen Edrich; Tongsheng Zhang, both of Neu-Ulm, Germany

[73] Assignee: Zentralinstitut fur Biomedizinische Technik Universitat Ulm, Germany

[21] Appl. No.: 08/738,818

[22] Filed: Oct. 28, 1996

[51] Int. Cl.[7] .................................................. A61N 1/00
[52] U.S. Cl. ............................................................ 600/13
[58] Field of Search .......................................... 600/9–15

[56] References Cited

U.S. PATENT DOCUMENTS

| | | | |
|---|---|---|---|
| 4,616,629 | 10/1986 | Moore | 600/13 |
| 4,672,951 | 6/1987 | Welch | 600/14 |
| 4,994,015 | 2/1991 | Cadwell . | |
| 5,047,005 | 9/1991 | Cadwell | 600/13 |
| 5,061,234 | 10/1991 | Chaney | 600/14 |
| 5,116,304 | 5/1992 | Cadwell | 600/13 |
| 5,267,938 | 12/1993 | Konotchick | 600/9 |
| 5,476,438 | 12/1995 | Edrich et al. | 600/2 |
| 5,496,258 | 3/1996 | Anninos et al. | 600/13 |
| 5,725,471 | 3/1998 | Davey et al. | 600/13 |
| 5,738,625 | 4/1998 | Glade | 600/9 |
| 5,766,124 | 6/1998 | Polson | 600/13 |
| 5,769,778 | 6/1998 | Abrams et al. | 600/14 |

FOREIGN PATENT DOCUMENTS 2 278 783   12/1994   United Kingdom .

OTHER PUBLICATIONS

International Search Report, Filed in PCT/EP 96/01759, Apr. 26, 1996.

Anthony T. Barker, "An Introduction to the Basic Principles of Magnetic Nerve Stimulation," *J. of Clinical Neurophysiology*, vol. 8, No. 1, pp. 26–37 (1991).

David Cohen et al., "Developing a More Focal Magnetic Simulator. Part I: Some Basic Principles," *J. of Clinical Neurophysiology*, vol. 8, No. 1, pp. 102–111 (1991).

Kazutomo Yunokuchi et al., "Developing a More Focal Magnetic Simulator. Part II: Fabricating Coils and Measuring Induced Current Distributions," *J. of Clinical Neurophysiology*, vol. 8, No. 1, pp. 112–120 (1991).

Bruce A. Evans, "Magnetic Stimulation of the Peripheral Nervous System," *J. of Clinical Neurophysiology*, vol. 8, No. 1, pp. 77–84 (1991).

J. Edrich et al., "Neuromagnetic Stimulation Using Ultrasound Focusing: Principles, Limitations, and Potential Applications," *Proc. 27th Ann. Meet. Biomed. Eng. Graz.*, vol. 38, pp. 415–416 (1993).

S. Ueno et al., "Localized stimulation of neural tissues in the brain by means of a paired configuration of time–varying magnetic fields," *J. Appl. Phys.*, vol. 64, No. 10, pp. 5862–5864 (Nov. 15, 1988).

Reza Jalinous, "Technical and Practical Aspects of Magnetic Nerve Stimulation," *J. of Clinical Neurophysiology*, vol. 8, No. 1, pp. 10–23 (1991).

H. Eaton, "Electric field induced in spherical volume conductor from arbitrary coils: application to magnetic stimulation and MEG," *Medical & Biological Engineering & Computing*, pp. 433–440 (Jul. 1992).

(List continued on next page.)

*Primary Examiner*—Francis J. Jaworski
*Attorney, Agent, or Firm*—Dorr, Carson, Sloan & Birney, P.C.

[57] ABSTRACT

A method and coil apparatus for magnetically stimulating and detecting neural systems both in animals and in humans is disclosed that can provide a peak electric field focus into a selected and electronically adjustable subcutaneous target region of neuronal tissue. Currents in adjacent coils are directed in opposite directions to provide a near surface cancellation of electric fields while producing a peak electric field focus in the target region. The depth and position of the peak electric field focus can be adjusted and steered. In one embodiment, the target volume of neuronal tissue is stimulated with a peak of maximum electric field energy. In a second embodiment, the nerve currents in the target volume are detected.

18 Claims, 8 Drawing Sheets

OTHER PUBLICATIONS

Anthony Murro et al., "A Model For Focal Magnetic Brain Stimulation," *Int. J. Biomed. Comput.*, vol. 31, pp. 37–43 (1992).

Bradley J. Roth et al., "A Model of the Stimulation of a Nerve Fiber by Electromagnetic Induction," *IEEE Transactions on Biomedical Engineering*, vol. 37, No. 6, pp. 588–597 (Jun. 1990).

Peter J. Basser et al., "The Activating Function for Magnetic Stimulation Derived From a Three–Dimensional Volume Conductor Model," *IEEE Transactions on Biomedical Engineering*, vol. 39, No. 11, pp. 1207–1211 (Nov. 1992).

Karu P. Esselle et al., "Neural Stimulation with Magnetic Fields: Analysis of Induced Electric Fields," *IEEE Transactions on Biomedical Engineering*, vol. 39, No. 7, pp. 693–699 (Jul. 1992).

Karu P. Esselle et al., "Cylindrical Tissue Model for Magnetic Field Stimulation of Neurons: Effects of Coil Geometry," *IEEE Transactions on Biomedical Engineering*, vol. 42, No. 9, pp. 934–941 (Sep. 1995).

Christian Bischoff et al., "The Value of Magnetic Stimulation in the Diagnosis of Radiculopathies," *Muscle & Nerve*, vol. 16, pp. 154–161 (Feb. 1993).

Gerhard M. Baule, "Biomagnetic Instrumentation of Heart," *New York State Journal of Medicine*, pp. 3095–3100 (Dec. 1, 1967).

James E. Zimmerman, "SQUID instruments and shielding for low–level magnetic measurements," *Journal of Applied Physics*, vol. 48, No. 2, pp. 702–710 (Feb. 1977).

Martin Reite et al., "The Human Magnetoncephalogram: Some EEG and Related Correlations," *Electroencephalography and Clinical Neurophysiology*, vol. 40, pp. 59–66 (1976).

S.J. Williamson et al., "Biomagnetism," *J. Magnetism Magn. Mat.*, vol. 22, pp. 146–201 (1981).

S.N. Erné et al. (ed.), "Biomagnetism," *Proceedings Third Int'l Workshop on Biomagnetism Berlin (West)*, pp. Title p.–137 (1981).

P. Weismüller et al., "Biomagnetic Noninvasive Localization of Accessory Pathways in Wolff–Parkinson–White Syndrome," *Pace*, vol. 14, Part II, pp. 1961–1965 (Nov. 1965).

R. Kristeva–Feige et al., "Movement–Related Activity During Local Anesthesia: A Neuromagnetic Study," *Tenth Int'l Conference on Biomagnetism, Biomag 96 Abstracts*, p. 268 (Feb. 16–21, 1996).

Detail A

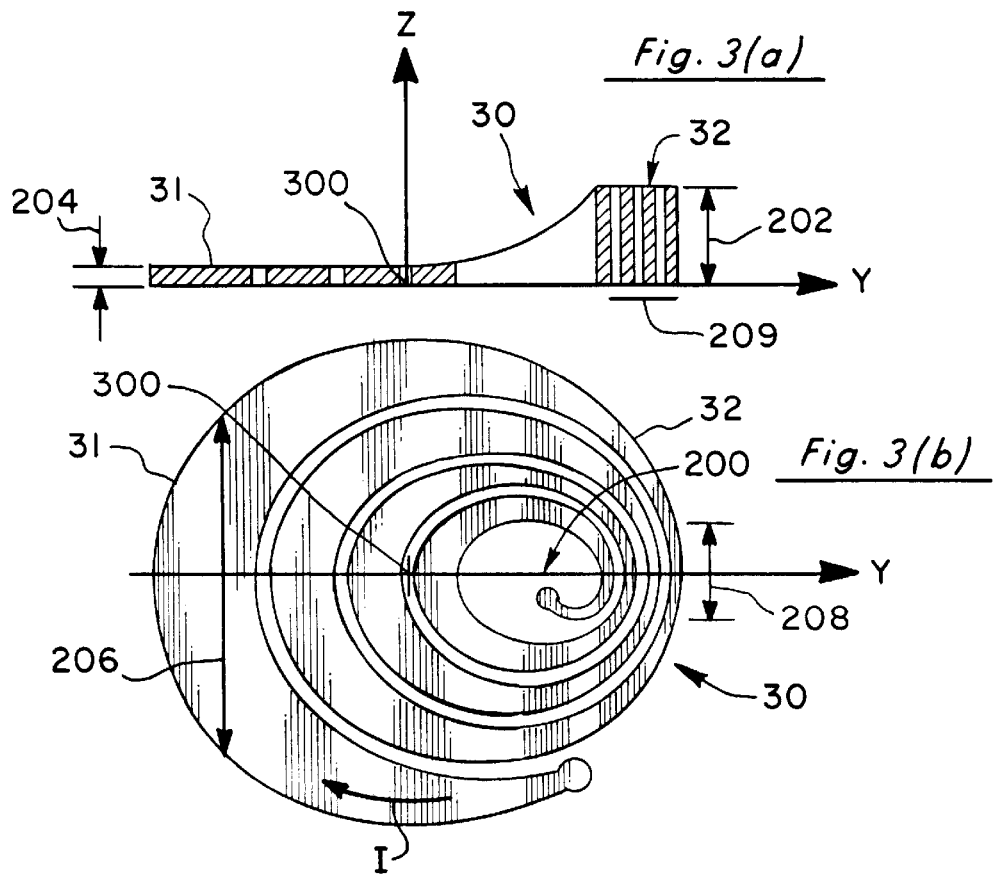
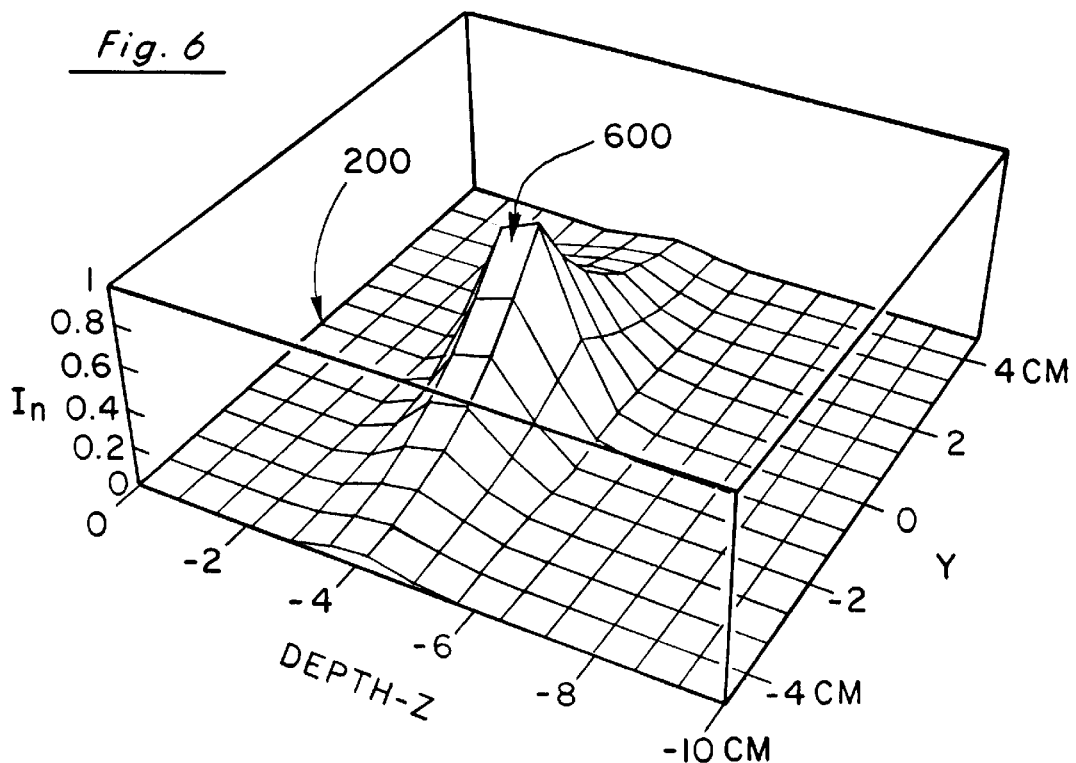

METHOD AND APPARATUS FOR FOCUSED NEUROMAGNETIC STIMULATION AND DETECTION

BACKGROUND OF THE INVENTION

1. Field of the Invention

This invention relates to neuron stimulation and detection, and, more particularly, to neuromagnetic coil systems and their associated drive circuitry for focused neuron stimulation in selected and electronically controllable subcutaneous regions, as well as for more focused neuromagnetic detection, for example, of biosignals in magnetoencephalography and magnetocardiography.

2. Statement of the Problem a) Neuromagnetic Stimulation Methods and apparatuses utilizing magnetic stimulation in neural tissues have gained importance for experimentally evoking responses in animals and for some clinical applications. "An Introduction to the Basic Principles of Magnetic Nerve Stimulation" by Barker, "Journal of Clinical Neurophysiology", Vol. 8, No. 1, pp. 26–37, 1991, sets forth the basic principles involving magnetic nerve stimulation. See, also, U.S. Pat. No. 5,047,005 to Cadwell entitled "Method and Apparatus for Magnetically Stimulating Neurons" and U.S. Pat. No. 5,061,234 to Chaney entitled "Magnetic Neural Stimulator for Neurophysiology." As compared to conventional electrical stimulation, such prior magnetic approaches exhibit a number of attractive characteristics. For example, they are non-contacting and noninvasive, they are relatively pain-free, and, most importantly, they can stimulate deeper, normally nonaccessible nerves.

The following references on neuromagnetic stimulation indicate that there is a variety of reports on experimental results utilizing phantoms, animals, and even humans.

In "Developing a More Focal Magnetic Stimulator. Part I: Some Basic Principles", by Cohen and Cuffin, Journal of Clinical Neurophysiology, Vol. 8, No. 1, 1991, pp. 102–111 sets forth a discussion of the magnetic stimulation created by a circular coil parallel to, a circular coil orthogonal to, and a figure-8 coil parallel to the surface of tissue. Cohen et al., recognizes the need to obtain "true focusing" and the lack of any present design to achieve this "true focus." (See page 106). Cohen criticizes the figure-8 coil as being "very inefficient although it exhibited an improvement and focality with decreasing diameter down to 1 cm. In Yunokuchi and Cohen, "Developing A More Focal Magnetic Stimulator. Part II: Fabricating Coils and Measuring Induced Current Distributions", Journal of Clinical Neurophysiology, Vol. 8, No. 1, pp. 112–120, 1991, actual fabricated coils were evaluated.

In "Magnetic Stimulation of the Peripheral Nervous System" by Evans, Journal of Clinical Neurophysiology, Vol. 8, No. 1, 1991, pp. 77–84, the use of a coil in the shape of a butterfly is examined. However, Evans recognizes that when stimulating deeper nerves the patient may experience local pain due to the high current densities involved.

U.S. Pat. No. 5,476,438 entitled "Method and Apparatus for Neuromagnetic Stimulation" and the related article "Neuromagnetic Stimulation Using Ultrasound Focusing: Principles, Limitations and Potential Applications" 27th Annual Meeting Biomedical Engineering Graz., Vol. 38, pp. 415–416, (1993) both by the present inventors set forth an approach using a focused beam of ultrasonic waves interacting into the magnetic field region to produce a subcutaneous focus stimulation having a focal diameter of approximately 1 cm.

Other publications in this field are: S. Ueno et al., "Localized Stimulation of Neural Tissues in the Brain by Means of a Paired Configuration of Time-varying Magnetic Fields", J. Appl. Phys., Vol 64, No. 10, pp. 5862–5864, 1998; Reza Jalinous, "Technical and Practical Aspects of Magnetic Nerve Stimulation", Journal of Clinical Neurophysiology., Vol. 8, No. 1, pp. 10–25 1991; H. Eaton, "Electric Field Induced in a Spherical Volume Conductor from Arbitrary Coils: Application to Magnetic Stimulation and MEG", Med. & Biol. Eng. & Comp., Vol. 30, pp. 433–440, 1992; Anthony Murro et al., "A Model for Focal Magnetic Brain Stimulation", International Journal of Biomed. Comput., Vol. 31, pp. 37–43, 1992; Bradley J. Roth et al., "A model of the Stimulation of a Nerve Fiber by Electromagnetic Induction", IEEE Trans. on Biomed. Eng., Vol. 37, No. 6, 1990; Peter J. Basser et al., "The Activating Function for Magnetic Stimulation Derived from a Three-Dimensional Volume Conductor Model", IEEE Trans. on Biomed. Eng., Vol. 39, No. 11, pp. 1207–1210 1992; Karu P. Esselle et al., "Neural Stimulation with Magnetic Fields: Analysis of Induced Electric Fields", IEEE Trans. on Biomed. Eng., Vol. 39, No. 7, pp. 693–700 July 1992; Karu P. Esselle et al., "Cylindrical Tissue Model for Magnetic Field Stimulation of Neurons: Effects of Coil Geometry", IEEE Trans. on Biomed. Eng., Vol., 42, No. 9, pp. 934–941 September 1995; C. Bischoff et al., "The Value of Magnetic Stimulation in the Diagnosis of Radiculopathies", Muscle Nerve, Vol. 16, pp. 154–161, 1993. The above papers on modeling and simulations of the effects of magnetic stimulation also explore the various mechanisms involved. They show that the induced electric field intensity plays an important role in exciting short nerves, while first order spatial derivatives of electric fields, which are induced along the nerves, act as activating functions towards their excitation. As compared to simple circular coils, the "figure-of-eight" coils (also called "Double-D" or "Butterfly"), the coils with sharp corners, and the "slinky" coils have been reported to yield somewhat improved performance for certain applications.

Yet all of these prior art coil configurations share one main functional disadvantage: they produce maximum field intensity in the surface regions of the tissue including the region that is closest to the coils and considerably lower field intensities in the desired subsurface tissue locations. In other words, they cannot truly focus into deeper subsurface volumes of neuronal tissues as required by most users in animal and general neurophysiological research, as well as in clinical applications. To achieve a desired field intensity at the desired depth, their coils may overheat in high field condition and may overstimulate and overheat superficial tissues. A need exists to overcome these problems and to provide a coil design that provides a peak electric field in a target volume of neuronal tissue thereby increasing focality. A further need exists to control the depth of the peak and to control the orientation of the exciting field vector in the peak.

b) Neuromagnetic Detection—There is a certain similarity, although not simple reciprocity of the stimulation mechanism of nerve tissues by coils, and the inverse, e.g., the detection by coils of the fields naturally emitted by nerve tissues. The latter one is, for example, done in magnetoencephalography (MEG) or in magnetocardiography (MCG) (G. M. Baule, N.Y. State J. Med., 67, p. 3095, 1967; J. E. Zimmerman, J. Appl. Physics 48, p. 702, 1977; M. Reite, J. E. Zimmerman, J. Edrich, H. Zimmerman, Electroenc. Clin. Neurophysiol. 40. p. 59, 1976; W. J. Williamson, et al., J. Magnetism and Magn. Mat. 22, p. 129, 1981; S. N. Erné et al., ed., Biomagnetism, W. D. Gruyter, Berlin, 1981; P.

Weismüller, J. Edrich et al., PACE Vol. 14 p. 1961, 1991; R. Kristeva-Feige, S. N. Erné, J. Edrich, et al., Abstr. BIOMAG 96, p. 268, 1996.

Therefore it can be expected that some, although not all, of the above mentioned problems associated with stimulation also occur with biomagnetic detection. In fact, the problems due to limited spatial localization accuracy of detecting current sources associated with neural activities in the brain and with the electrophysiological activities of the heart are presently of acute concern. (Abstr./Proc. BIOMAG 96; Santa Fe, pp. 1–340, 1996). Many of the industrial and development groups optimizing MEG and MCG (for functional imaging in neurophysiological or clinical application) are presently trying to overcome the localization problems of conventional biomagnetic coil systems by using so-called multichannel systems. These approaches also use many coils placed side-by-side over the nerve tissue to be measured. For example 150 coils or coil systems, are used in helmet like structures for the brain (MEG) or 55 coils or coil systems are used in planar, circular arrays for the heart (MCG). In contrast to stimulation with fields in the Tesla range, here the fields produced by the nerve currents are of the order of $10^{-10}$ Tesla or less, i.e., very weak, although still accurately measurable using conventional superconducting coils and Josephson detectors. Depth localization or subcutaneous current sources or dipoles are facilitated and made more accurate by using the above multi-coil/multichannel approaches. However, the accuracy is still very marginal for many neurophysiological and clinical applications, in particular, if comparison with structural imaging methods, such as MRI and CAT, is needed, as is required by many users. Focusing into deeper tissue regions is, for example, especially important for the relatively deep current sources of the endocard using MCG. Here and also in MEG applications (preoperative localizations of epileptic foci, schizophrenia etc.), the so-called "biological noise", is also a major source of problems. It is caused by the pickup and detection of unwanted fields due to nerve currents in volumes that are not of interest, but are, unfortunately, included because of the coarse volume resolution of conventional coils. Similar to the stimulating coils, here the inductance plays a major role in the signal-sensitivity of coils (J. E. Zimmerman, J. Appl. Phys. 48, p. 703, 1977). All of the above problems point at the need for improved coils or coils system with significantly higher spatial resolution at subcutaneous depths that are of interest for most neurophysiological and clinical applications.

A need exists for a coil system that focuses on a target volume or region of neuronal subcutaneous tissue. A need also exists to provide electronic weighting of biomagnetically detected coil currents and the determination of the direction of vectorial nerve current dipoles.

In one application, the coil design stimulates the target volume of neuronal tissue with a peak of electric field energy. In a second application, the coil design detects in the target volume of neuronal tissue electrical fields generated by nerve currents.

3. Solution to the Problem

It is an objective of this invention to provide an effective method and apparatus for focusing on a target region of subcutaneous nerve tissue for neuromagnetic stimulation or for biomagnetic detection of naturally occurring nerve currents.

It is a further objective of the invention to provide a method and apparatus to avoid the focusing problems and to reduce overheating of coils of conventional magnetic stimulators under high field conditions and to significantly reduce the problems in biomagnetic detection that are caused by noise and coarse spatial resolution.

It is a still further objective of the invention to provide a method and apparatus for neuromagnetic stimulation that provide a more focused stimulation of selected subcutaneous nerve tissue regions without over stimulating and overheating superficial tissues and, similarly, provide a more focused low noise detection of deeper biomagnetic signals.

It is still a further objective of the present invention to provide a method and apparatus for neuromagnetic stimulation that controls the depth and the orientation of the exciting field vectors and for biomagnetic detection that electronically weighs the detected currents and determines the direction of vectorial nerve current dipoles.

SUMMARY OF THE INVENTION

According to this invention a new method and apparatus are provided for stimulating excitable tissues selectively by magnetically induced currents that are produced by a two- or four-channel electronic circuit and preferably by one or two pairs of in-plane or, approximate orthogonal, excentric coils, and, similarly for detecting more selectively biomagnetic nerve signals.

The larger the diameter of a coil, the deeper the induced electric field can penetrate into the tissue. The maximum field of a conventional circular coil which is placed in parallel to and above a tissue surface occurs in parallel rings roughly underneath the circumference of the coil. These rings increase in diameter, while their inherent field strength decreases with increasing tissue depth resulting in a relatively poor focality for conventional circular coils. Although a stimulating coil placed orthogonal to and above the tissue surface produces a more focal field distribution in tissues that are close to the coil, the field intensity decreases more rapidly with distance from the coil than a horizontal stimulating coil. When placing horizontal and vertical coils orthogonally closely together, and controlling their driving currents properly according to this invention, the apparatus of the present invention obtains a resultant induced electric field which forms a peak value at a desired tissue depth while at the same time the induced field in the near field region, (e.g. at or slightly below the tissue surface) is minimized out because of mutually opposing fields. This contrasts to the situation with conventional coils where peaking of the field intensity occurs at the tissue surface, and fields deeper inside the tissue are considerably lower. Therefore the apparatus of the present invention can stimulate excitable tissues at much deeper subcutaneous depths without over stimulating the shallower regions as is the case with the conventional coil systems.

Because of the electromagnetically reciprocal relationship between the case of irradiation/stimulation into the tissue, and the case of detection of naturally emitted radiation from tissue, the coil system and method can detect nerve current sources at much deeper subcutaneous depths without the added, unwanted noise contributions from shallower regions as is the case with conventional coil systems of biomagnetic magnetometers and gradiometers.

This leads to a substantial improvement of the focality of magnetic stimulation while at the same time removing the main obstacle regarding a more intensified stimulation in deeper tissue regions often required by users for neurophysiological experiments or for clinical applications. This also leads to a substantially improved biomagnetic detection at subcutaneous depths often required by users for neurophysiological experiments or clinical applications.

Electronic control of the coil currents allows rapid adjustment of the depth of the above mentioned subcutaneous focus of excitation and also of the orientation of the exciting field vector. Similarly, electronic weighting of the biomagnetically detected coil currents allows rapid adjustment of the subcutaneous detection focus, and of the determination of the direction of vectorial nerve current dipoles.

Special excentric forms and cross-sections of the invented coil systems result in less extraneous, unwanted fields, higher driving coil currents and/or higher pulse repetition rates while at the same time reducing overheating of coils as compared to conventional coils. Similarly, excentric forms and cross-sections of the invented coil systems detect fewer extraneous, unwanted nerve current dipoles, and result in a lower system noise, e.g., improved biomagnetic signal detection.

A multi-channel electronic circuits control and drive the focusing stimulator and detector coil systems of the present invention.

BRIEF DESCRIPTION OF THE DRAWING

FIG. 2d illustrates the steering of the peak focus region;

FIG. 3 depicts one embodiment of the excentric coil of the present invention having four turns;

FIG. 6 illustrates the currents induced or detected in tissue by utilizing two orthogonal coils;

DETAILED DESCRIPTION OF THE INVENTION

1. Prior Art

Figure 1A:
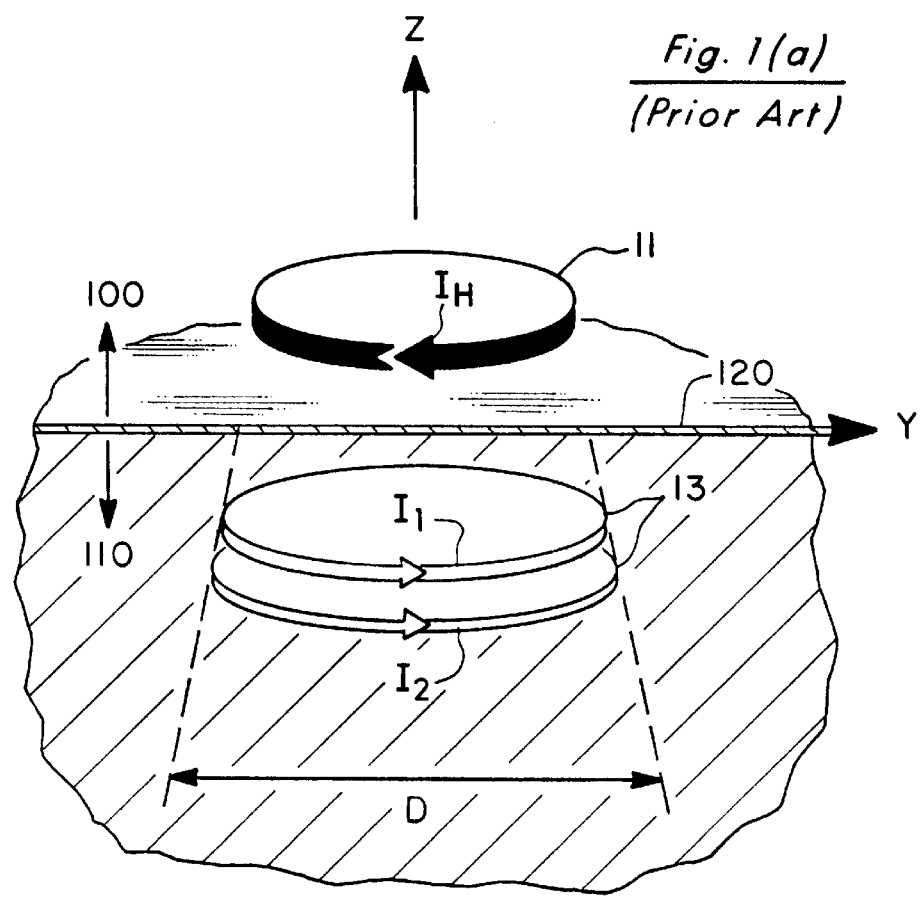
FIGS. 1a and 1b (prior art) are a schematic diagram of horizontally oriented currents induced for stimulation of nerves in tissue or biomagnetically detected from nerves using a horizontal coil or a vertical coil.
Figure 1B:
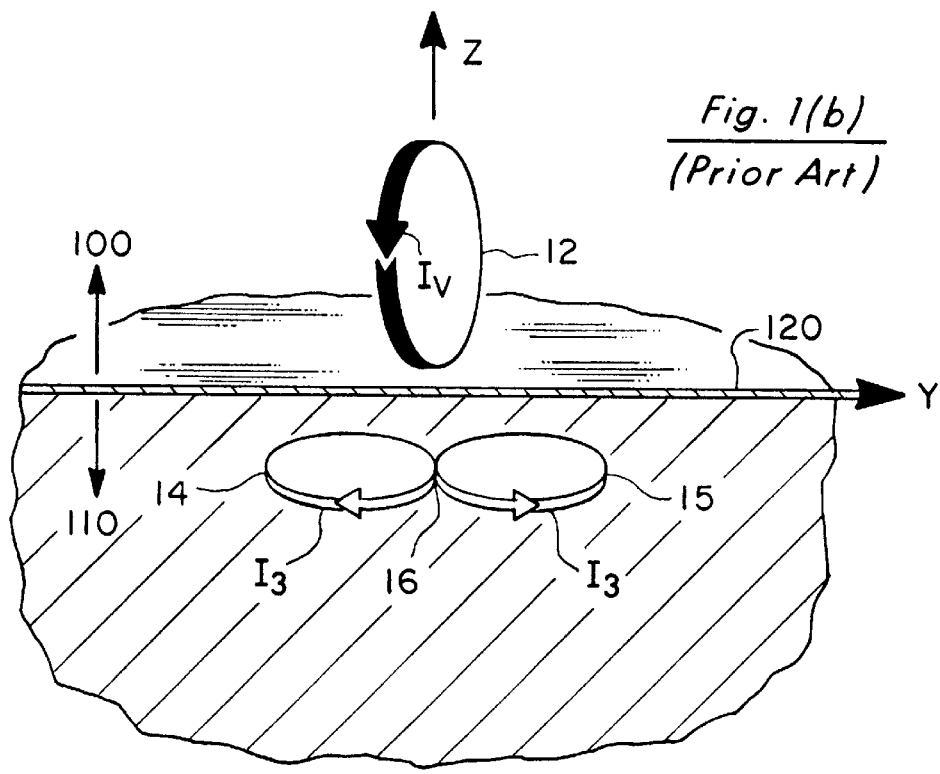

FIG. 1 illustrates conventional coils that are horizontally (coil 11 in FIG. 1a) or vertically (coil 12 in FIG. 1b) positioned in air 100 over semi-infinite planar tissue 110. The tissue 110 has a surface 120. The highest tissue currents 13 induced by current $I_H$ (or detected in the horizontal coil 11) can be found in tissue 110 underneath the coil 11, roughly along the circumference of the coil 11 near the surface 120. With increasing tissue depth the diameter D of these current rings 13 increases and the current intensity decreases ($I_2<I_1$). As FIG. 1b illustrates, this is also true for the current rings 14, 15 induced in the tissue 110 by the current $I_V$ of the vertical coil 12 (or biomagnetically detected in it.) These current rings are two side-by-side current loops 14 and 15. They are joined at location 16 which exhibits a relatively high concentration of current intensity ($I_3+I_3$) because of the geometrical superposition of the two current rings 14 and 15. This location 16 underneath the vertical coil 12 therefore serves as the focality region for stimulation (or detection) because of its field concentrating characteristics. The horizontal coil 11, however, produces larger absolute current densities in deeper tissues than the vertical coil 12, indicating that horizontal coils can more effectively stimulate deeper neuronal tissues (or biomagnetically detect signals therefrom.) It is to be understood that the actual design of the physical coils 11 and 12 for stimulation is different than that for detection as pointed out above in the Background section. The function, however, is the same. Nerve currents in the region of $I_1$ and $I_2$ produce a current $I_H$ in coil 11 and nerve currents in the region of $I_{14}$ and $I_{15}$ produce a current $I_V$ in coil 12. These detected nerve currents are much weaker than the induced nerve currents.

The above prior art coil configurations utilizing a Butterfly, Double D, sharp corners, or slinky design produce higher concentrations of current intensity although only for relatively shallow tissue depths. They also exhibit other disadvantages which were already pointed out above.

The design of coils 11 and 12, the electronic circuitry for driving coils 11 and 12, and the currents and voltages are well known in the art and are set forth in the above references. For example, Chaney discloses a 2 cm diameter disk-shaped stimulation coil wound in a helical manner using flat insulated wire having a rectangular cross-section of 0.75 cm by 1.0 mm. The thickness of the coil is 0.75 cm so the wire is coiled on its thin edge. This coil design produces a stronger magnetic field near the center of the coil. Water cooling tubes may be used to cool the coil as the maximum current through the coil is 6,000 amps. Likewise, the design of coils 11 for current detection and the associated sensing circuitry are well known in MEG and MCG applications.

2. H-V Design: Two Coils

Figure 2A:
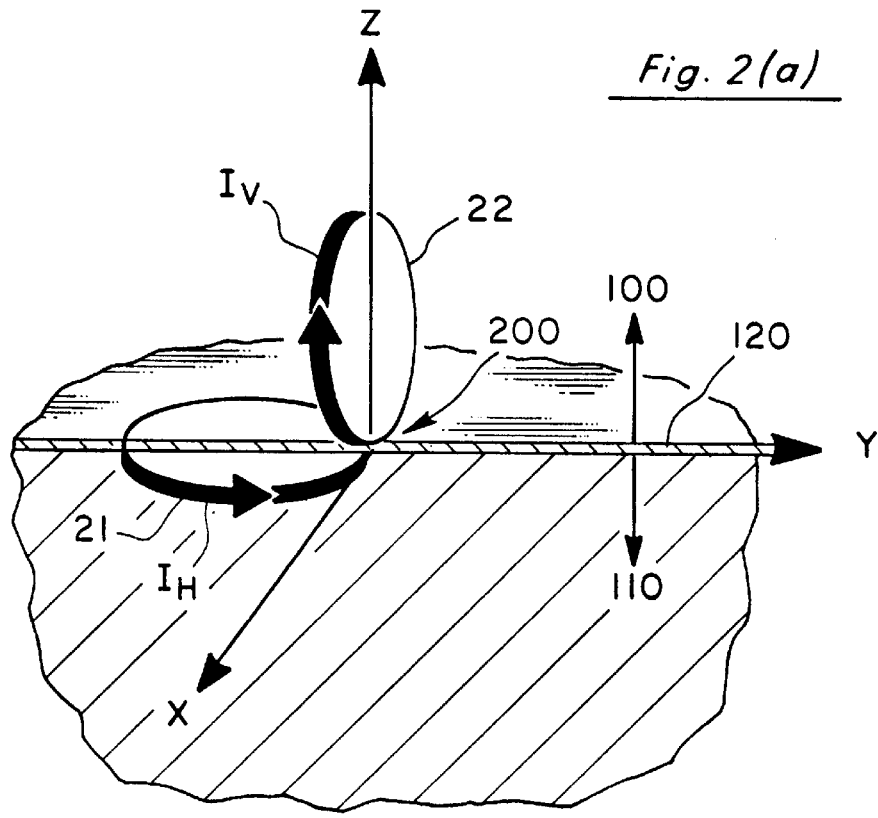
FIG. 2a illustrates one embodiment of the two coil arrangement of the present invention.

To overcome the problems and limitations of conventional coil configurations, the coil apparatus of FIG. 2a is presented in accordance with this invention. One embodiment of the present invention comprises the substantially horizontal (H) coil 21 and the substantially vertical (V) coil 22 which are separately driven by opposing currents ($I_H$ and $I_V$) shown by arrows (or are oppositely connected for biomagnetic current detection.) These coils 21 and 22 nearly touch each other in the region 200 (i.e., at x, y, z=0) near the surface 120 and remain separate electrical circuits. Coils 21 and 22 can be of dimension comparable to the prior art coils of FIG. 1.

Figure 2B:
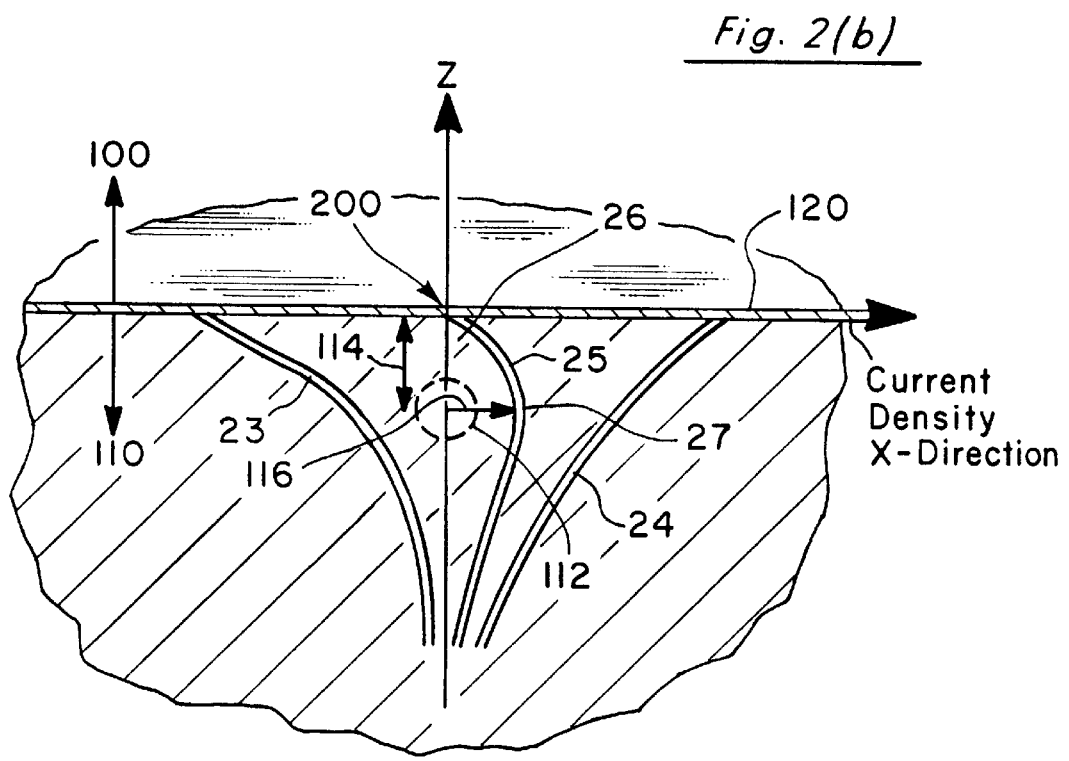
FIG. 2b shows the horizontally oriented current densities in tissue produced or detected by the horizontal and vertical coils individually, and the resultant current density caused by their superposition which results in the focused region.

FIG. 2b shows the induced or detected current densities 23 and 24 in the x-direction due to the substantially vertical and the substantially horizontal coils 22 and 21 in FIG. 2a, respectively. In FIG. 2b, the resultant current density 25 in the x-direction represents the linear superposition of the curves 23 and 24 which produces the desired field cancellation in the region 26 of shallow tissue depth (around z=y=z=0), and, most importantly, peak electric field focus 27 which is the targeted subcutaneously focusing region 112.

The following are preferred value ranges for the coils 21 and 22 of FIG. 2a:

coil diameter: 1–10 cm
number of turns: 1–10 turns
cross-sectional area of wire: 1–10 mm$^2$ In a typical example of one embodiment for the coils 21 and 22 of FIG. 2a, the values are:

coil diameter: 5 cm
turns: 5

The current is applied to coils 21 and 22 in a pulse width of 100 msec and a value of 5000 amperes.

As shown in FIG. 2b, the peak electric field focus 27 (and, therefore, the targeted region 112) can be positioned to depth 114 and in intensity 116 by selectively adjusting the values for the currents $I_V$ and $I_H$. Greater current values for $I_V$ and $I_H$ result in deeper targeted regions 112. Varying the ratios of the currents $I_V$ and $I_H$ tailor the position (i.e., shape and intensity) of the peak 27.

The present invention is not limited by the orientation of the substantially vertical coil H. For example, some embodiments may orient this coil at 45° or 60°.

Figure 2C:
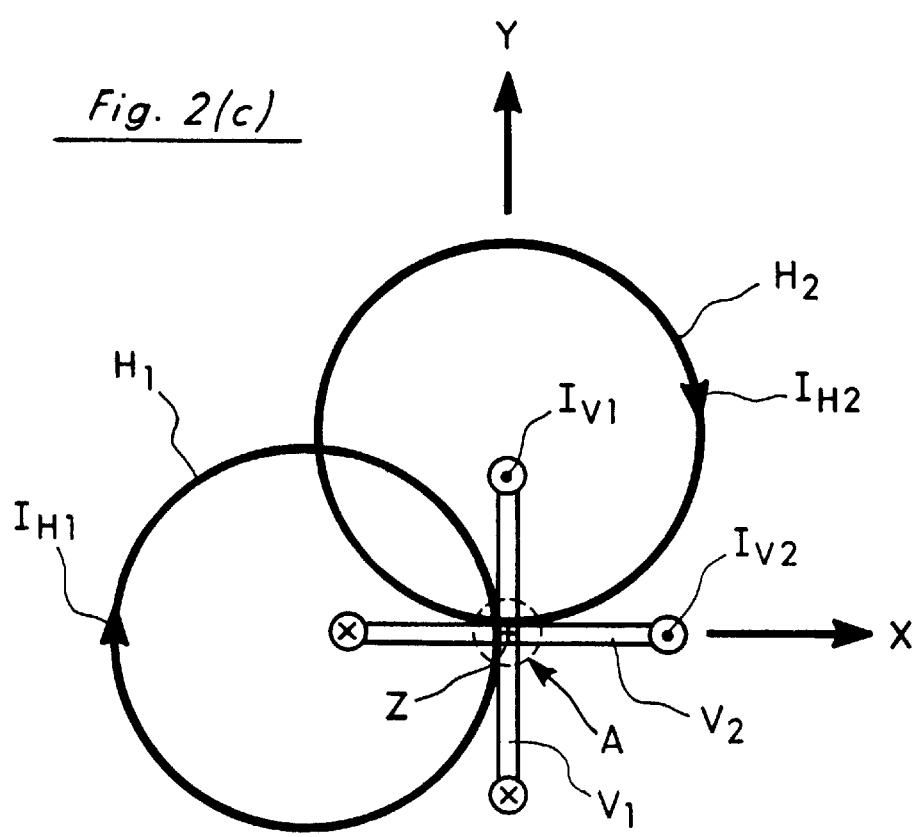
FIG. 2c shows an orthogonal four-coil configuration similar to FIG. 2a that can electronically rotate the excitation or detection vector, and also it subcutaneous depth.
Figure 2C:
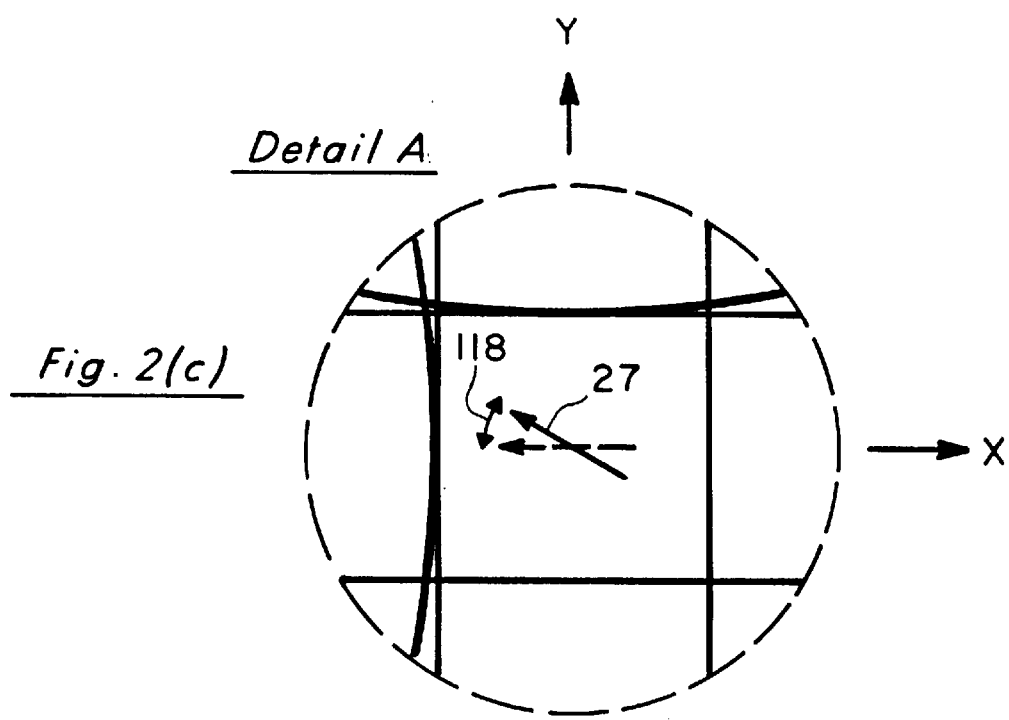

An extension of this invention contains two pairs of, for example, superposed orthogonal coils. All of them are joined at x=y=z=0; however, the vertical and horizontal coils are rotated by ninety degrees. It is to be understood, that the present invention is not limited by a ninety degree rotation. As opposed to the two-coil arrangement, the four-coil arrangement is not restricted to exciting (or detecting) only nerves oriented primarily in one single direction, e.g., in x-direction for the configuration of FIG. 2a, but it can produce neuronal excitation or detection in all possible directions in the x-y plane by means of electronically variable (or weighted) and event time scanned currents in each orthogonal coil pair. FIG. 2c illustrates, from top planar view, a four-coil configuration using two pairs ($H_1$-$V_1$ and $H_2$-$V_2$) coils. Each pair of coils can induce (or detect) subcutaneously focused currents in all directions of the X-Y plane where the direction is electronically adjustable by the coil currents (or their weight for detection). The steering 118 of the peak induced (or detected) current 27 in the x-y plane is illustrated in FIG. 2c. Steering 118 can occur at least two ways: electronically and mechanically. Making the value of $I_{H1}$ greater than the value of $I_{H2}$ orients the vector direction closer to the y axis. Hence, by controlling the current values for $I_H$ a desired direction can be obtained through electronic steering. Or, the coils $H_1$-$V_1$ and $H_2$-$V_2$ can be rotated about z=0 to mechanically steer 118 peak 27. In either case, the peak 27 can be stationary or can be selectively moved. Variable depth of the peak along the z-axis can again be achieved by adjusting the ratio of $I_{H1}$ to $I_{V1}$.

As shown in FIG. 2, the coil apparatus of the present invention is configured to focus in a target volume 112 at a desired depth 114 in the x plane or in the x-y plane. In one embodiment, a focus 27 of desired maximum field intensity 116 is delivered to stimulate neuronal tissue in the targeted volume. In another embodiment nerve currents are detected in the targeted volume from neuronal tissue.

What is shown in FIG. 2 is a pair of adjacent coils with each coil in the pair having a separate electrical path and with current in the separate electrical paths in opposing directions. This design provides a peak electric field focus in the target region of the subcutaneous nerve tissue. In the stimulation embodiment, current is applied to the coils in opposing directions to product the peak electric field focus. In the detecting embodiment, current is received from the coils in opposing directions from nerve currents in the peak electric field focus.

3. Preferred Design of Horizontal Coil

The coil arrangement of FIG. 2a produces (or detects) other undesirable peak current densities in tissue regions below the coils, that are located farther away from the z-axis at least if conventional separate circular coils were utilized. The following design avoids this. FIG. 3 depicts an excentric coil 30 having four turns; it is shown in a cross-sectional view (FIG. 3a) and a top planar view (FIG. 3b). One embodiment of its coil wire is shown which utilizes a band (i.e., rectangular cross-section) which is broad and laid flat in the low-field region 31 and is oriented upright (i.e., narrow) in the high-field region 32. The excentric coil 30 in the high field region 32 is of height 202 with each turn on edge. The height 202 is several times the height 204 of the low field region 31 where each turn is laid flat. Furthermore, the width 206 of the first turn in the low field region 31 is several times the width 208 of the first turn in the high field region. These excentric relationships, as will be explained later, concentrate the resultant field about area 209. Other possible embodiments of this design include wires with circular cross-section. The current I is in the direction indicated.

Figure 4:
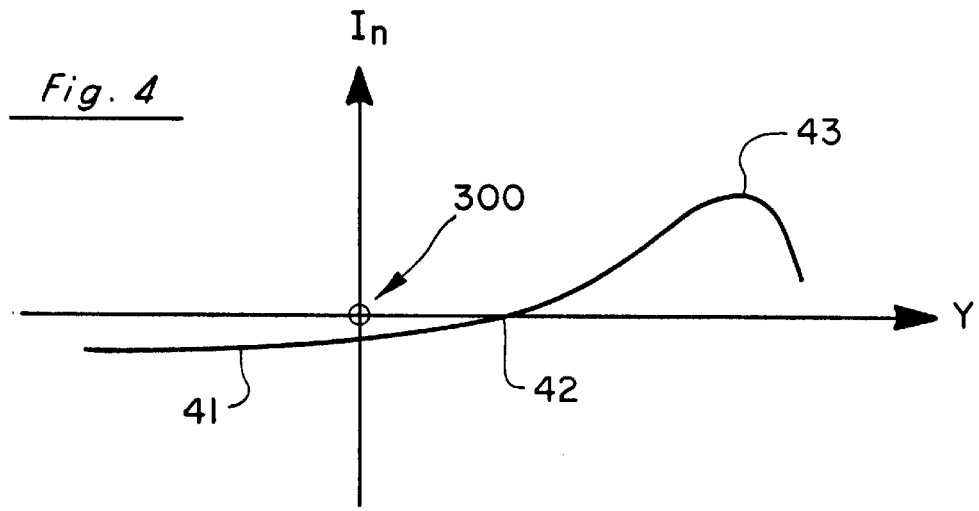
FIG. 4 illustrates the induced or detected current intensity of the excentric coil of FIG. 3.
Figure 5A:
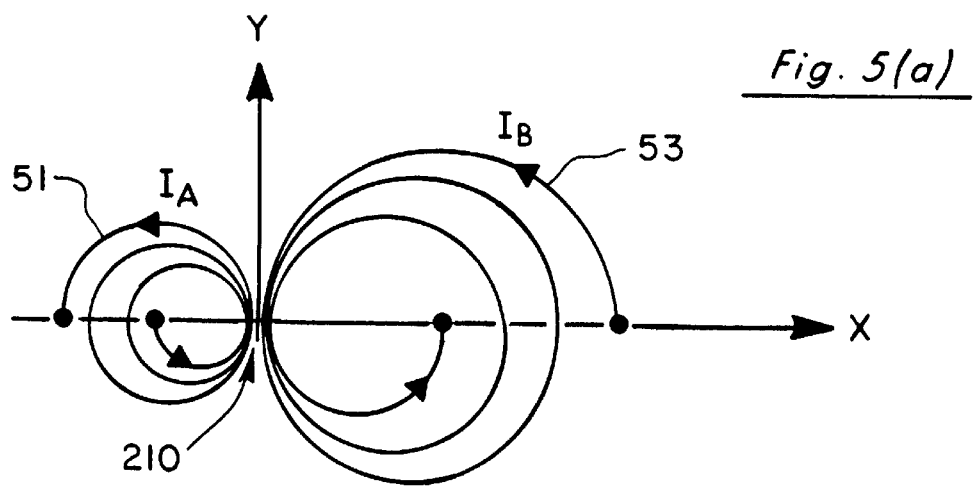
FIGS. 5a and 5b depict two other planar focusing embodiments of the two coil arrangements of the present invention which can produce or detect subcutaneous currents by means of excentric coils.
Figure 5B:
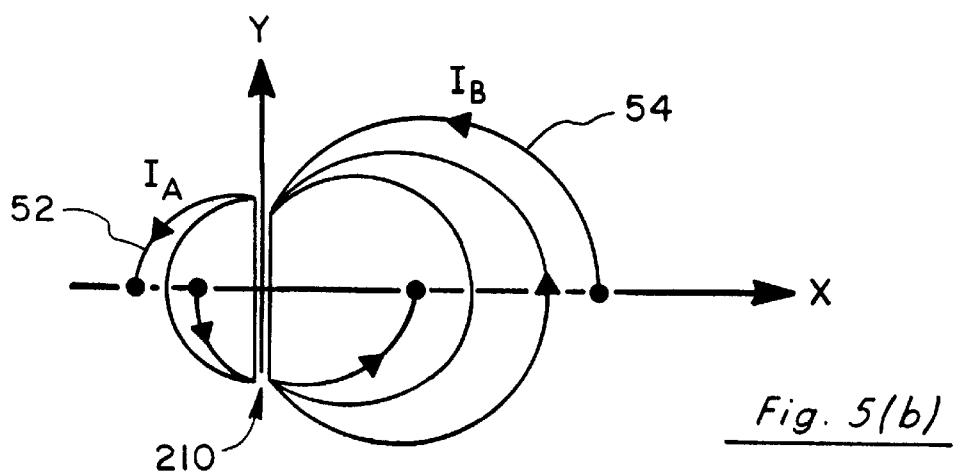
Figure 5C:
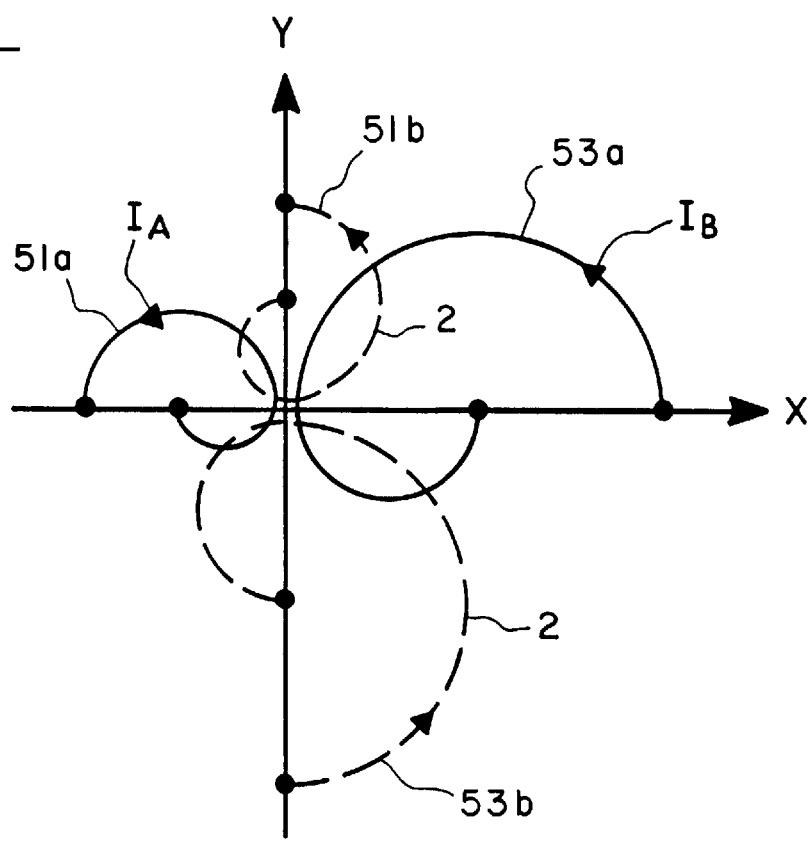
FIGS. 5c and 5d illustrate planar four-coil configurations similar to FIGS. 5a and 5b that can electronically rotate the excitation or detection vectors.
Figure 5D:
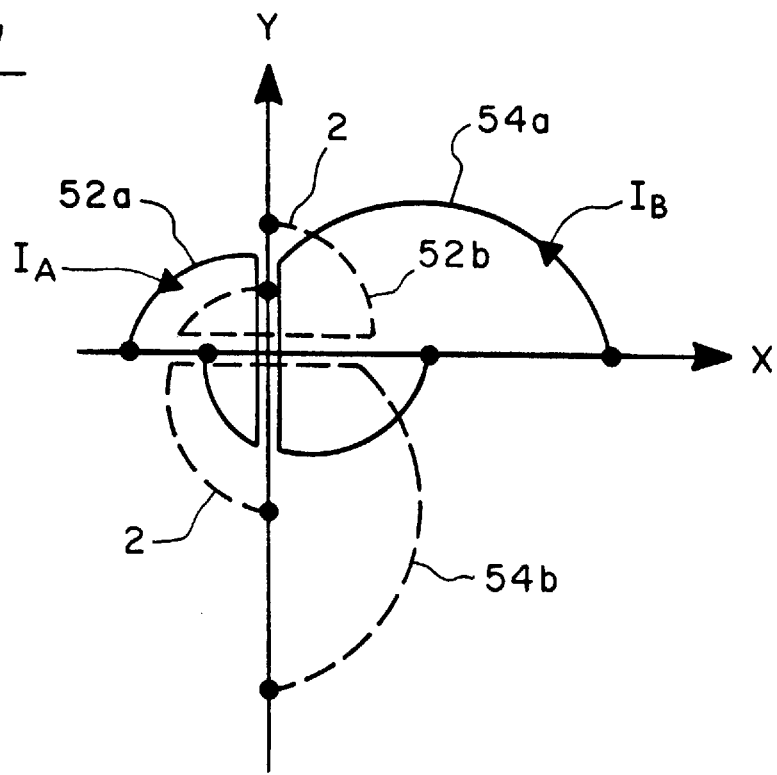

FIG. 4 shows the normalized current density $I_n$ induced (or detected) in a semi-infinite tissue placed underneath the coil in FIG. 3. The peak 43 corresponds to the high-field region 32 in FIG. 3, and the low-field 41 corresponds to the region 31 in FIG. 3. Note that zero crossing 42 is not located in the geometrical center 300 of the excentric coil, but close to the center of the coil hole 200 (FIG. 3b). This excentric configuration plays an important role in enhancing the focality. For stimulation it also improves the heat carrying characteristics of coil 30, e.g., for high field and current. The flat band construction of the excentric coil 30 significantly increases its heat radiation and/or cooling capability, which is a key performance parameter for these coils which are normally driven with high, pulsed currents (e.g., 6000 amps in 100 microsecond pulses).

The resistive heating of the conventional coils of FIG. 1 has severely limited their usefulness, particularly, for high fields and high repetition rates that are often required for practical cases in neurophysiological research and in clinical applications. As opposed to conventional coils, the excentric coil 30 with its good cooling capabilities may thus be used for cases requiring high fields and high pulse repetition rates. The excentric coil 30 also exhibits a significantly lower inductance, due to its smaller mutual inductance, its shorter turn length and its larger effective cross section of its wires. This, in turn, allows the production of even higher fields and/or pulse repetition rates, as compared to conventional coils. Therefore the electric fields induced in the nerve region of interest, and also the pulse repetition rate can be higher by factors as compared to conventional stimulators.

Because of electromagnetic reciprocity, biomagnetic detection of subcutaneous nerve currents benefits similarly form the improved focality, and lower inductance of the invented coil configurations by exhibiting several times better spatial resolution and lower extraneous noise as compared to conventional coils.

FIG. 6 shows a three dimensional plot of the current distribution induced (or biomagnetically detected) in subcutaneous tissue by two orthogonal coils (H-V coil of FIG. 2), each having four turns and a maximum diameter of 10 cm. The horizontal coil has an excentric shape similar to FIG. 3. These coils are closely joined in their high-field regions that result in the peaking or focusing effect on the z-axis at a depth of 4 cm or z=−4 cm. The location of this peak 600 of electric field intensity on the z-axis, i.e., the focusing depth, can electronically be varied as pointed above by varying or by weighting the coil currents. Point 200 in FIG. 6 corresponds to Point 200 in FIGS. 2a and 2b.

FIG. 6 illustrates the minimization of electric field intensity between the peak 600 and the surface of the tissue (z=0).

4. H-H Design: Two or Four Coils

FIG. 5 depicts four embodiments of two or four horizontal coils (H—H) which can also be utilized for subcutaneous focusing of the induced (or detected) currents by means of excentric coils. Again, the currents $I_A$ in the smaller coils 51 and 52 would have to be oriented in an opposing way in regard to the currents $I_B$ in the larger coils 53 and 54 as shown in FIGS. 5a and 5b in order to cancel the fields in the near surface regions of the tissue. With two straight coil sections closely joining each other 210 in the coil arrangement of FIG. 5b, this may be more suitable for exciting longer, straight nerve fibers or bundles in the targeted volume of neuronal tissue.

Similar to the above FIG. 2c, electronic steering of the direction of subcutaneously induced (or detected) current vectors can be accomplished by two identical one-turn coil pairs (51a-53a and 51b-53b for FIG. 5c and 52a-54a and 52b-54b for FIG. 5d) that are rotated around the z-axis at x=y=z=0, and superpositioned nearly in plane.

5. Stimulator System Design

Figure 7:
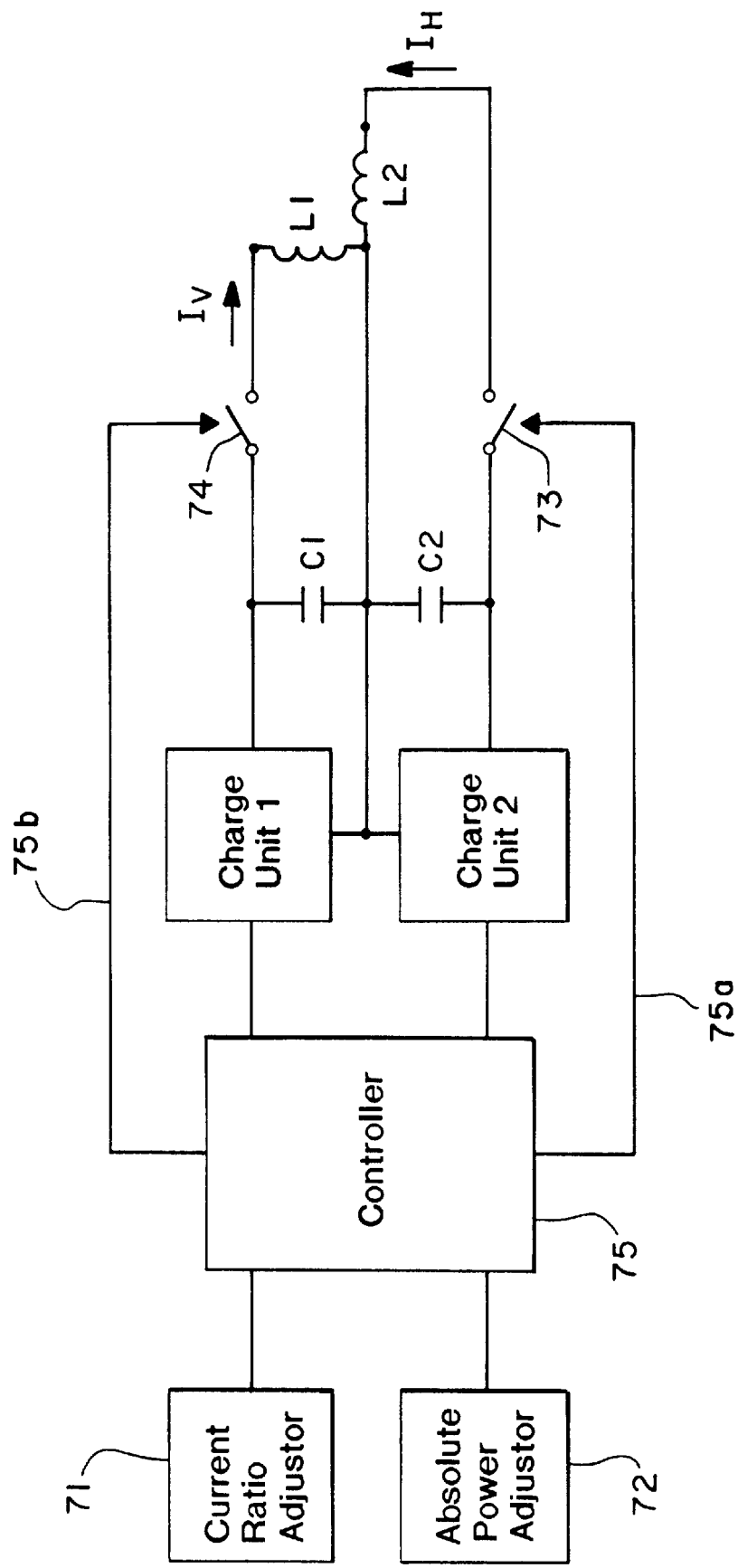
FIG. 7 illustrates the electronic block diagram of the magnetic stimulator of the present invention for controlling and discharging into the two-coil arrangements.

FIG. 7 shows the electronic circuit diagram of the magnetic stimulator of the present invention for the two-coil arrangements described above. A current ratio adjuster 71 sets the ratio of the two currents (for example, $I_H$ and $I_V$ of FIG. 2) driving the two coils $L_1$, $L_2$, while an absolute power adjuster 72 sets the amplitude of the sum of the two currents. The adjustment of the amplitude and ratio of the currents, as explained above, control the depth and the intensity of the peak. The two solid state discharge switches 73 and 74 are triggered synchronously by the controller 75 over lines 75a and 75b in order to ensure that the cancellation and the corresponding peaking/focusing effects happen simultaneously and in phase.

For the case of the four-coil configuration mentioned in the above description of FIG. 2 two identical circuits, like the one shown in FIG. 7, are synchronized, their absolute power adjusters linked by another sweepable ratio adjuster, and the switches connected to one pair of orthogonal coils each in order to produce the desired constant of time-sweepable rotation of the overall current vector exciting nerve fibers or bundles with the desired directionality (i.e., steering).

6. Biomagnetic Detector System Design

Figure 8:
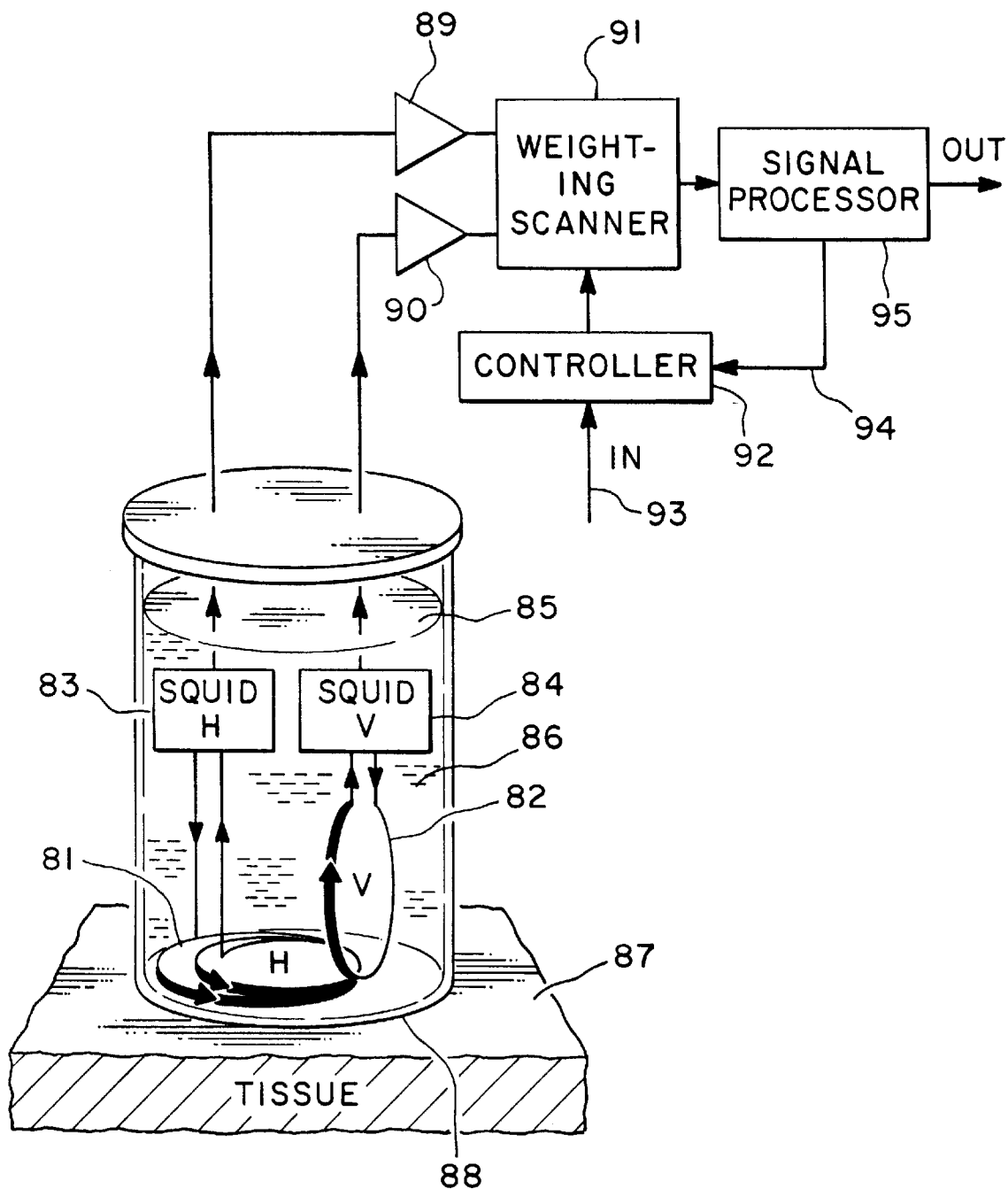
FIG. 8 illustrates the electronic block diagram of the special biomagnetic detector system of the present invention which controls the coil pairs for optimum surface cancellation and depth focusing.

FIG. 8 shows the electronic circuit and system design of a biomagnetic detector of the present invention illustrating, instead of multichannel systems, only a single channel sensor system, comprised of the invented H-V coil pair of one horizontal excentric coil 81 of two turns and one vertical circular coil 82 of one turn. The coils are, together with their corresponding conventional SQUID detectors 83 and 84, typically cooled inside a superinsulated vacuum dewar 85 using liquid helium 86 to a temperature of 4 K. The dewar is transparent to the low frequency biomagnetic fields emitted by the nerve current sources in the tissue 87 which is placed close to the bottom 88 of the dewar. The SQUID detectors 83 and 84 are connected with SQUID converters and amplifiers 89 and 90. Their outputs undergo, in the weighting scanner 91, processing in order to automatically achieve the surface field cancellation and the depth focusing described above. A controller 92 can manually 93 be controlled, and receives also feedback 94 from the output signal processor 95. Instead of the single orthogonal coil configurations the planar or vectorial configurations described above can be used too.

Furthermore several of these invented configurations can be combined to form standard axial or planar gradiometers in order to measure field derivatives and to more efficiently reject unwanted environmental field disturbances.

7. Method

A neuronal magnetic method is set forth in the drawings for providing a peak electric field focus 27 (FIG. 2b) in a target region 112 of subcutaneous nerve tissue 110. Under the teachings of the present invention the first and second coils in a pair are oriented on (which includes near) the surface 120 adjacent to each other. See FIG. 2a and FIGS. 5a and b. The current in the first coil is adjusted in a first direction which corresponds to a first electric field in the subcutaneous tissue. The current in the second coil is adjusted in a direction opposite to the first direction corresponding to a second electric field in the subcutaneous tissue. This is shown in FIGS. 2a and 2b for currents $I_V$, and $I_H$. In the first embodiment of stimulating nerve tissue in the target region 112 current is applied by the control of FIG. 7 to the coils in the opposing directions so as to produce the resulting electric field peak focus 27 in the target region 112. In the second embodiment of detection, currents are received in opposing directions from the first and second coils by the control of FIG. 8 to sense currents in the electric field peak focus 27 in the target region 112. In the case of stimulation, the electric field is minimized between the surface 120 and the target region 112 and in the case of detection, interfering or noise signals from tissue between the surface 120 and the target region 112 are minimized. Adjusting the ratio of the current in the first coil to the second coil positions the peak electric field focus 27 in the tissue and adjusting the magnitude of the current in the first coil and the second coil controls the depth 114 of the peak electric field focus 27 in the tissue.

The invention has been described with reference to the preferred embodiment. Modifications and alterations will occur to others upon a reading and understanding of this specification. It is intended to include all such modifications and alterations insofar as they come within the scope of the appended claims or the equivalents thereof.

We claim:

1. A neuromagnetic apparatus for focusing on a target region of subcutaneous nerve tissue below a surface of tissue, said neuromagnetic apparatus comprising:

a control circuit;

at least one pair of adjacent eccentric coils positioned in a region of adjacency and connected to said control circuit, each coil in said at least one pair of adjacent eccentric coils being positioned and controlled with respect to each other resulting in:

(a) a first broad low-field region produced near said surface of tissue; and (b) a second narrow high-field region produced below said surface of tissue, separate electrical paths connecting each of said at least one pair of adjacent eccentric coils to said control circuit and current in said separate electrical paths being in opposing directions in said region of adjacency of said at least one pair of adjacent eccentric coils, said at least one pair of adjacent eccentric coils synchronously-simultaneously operated, and said at least one pair of adjacent eccentric coils adapted to be placed near said surface tissue, at least said first broad low-field region and said second narrow high-field region interacting to provide a peak electric field focus in said target region of said subcutaneous nerve tissue and to cancel cutaneous fields near said region of adjacency and to reduce cutaneous fields elsewhere.

2. The neuromagnetic apparatus of claim 1 wherein at least one eccentric coil is oriented substantially parallel to and above said subcutaneous nerve tissue surface and said at least one pair of adjacent eccentric coils comprises at least one turn.

3. The neuromagnetic apparatus of claim 2 wherein said at least one turn of said at least one eccentric coil in the broad low field region has a predetermined height and a predetermined width, and wherein a first turn of said coil in said high field region has a height several times greater than said predetermined height and a width several times less than said predetermined width.

4. The neuromagnetic apparatus of claim 1 wherein said at least one pair of adjacent coils comprises:
a horizontal coil,
a vertical coil,
said horizontal coil located in a plane substantially parallel to said subcutaneous nerve tissue surface and said vertical coil oriented in a plane substantially orthogonal to said subcutaneous nerve tissue surface.

5. The neuromagnetic apparatus of claim 1 wherein said at least one pair of adjacent eccentric coils comprises a pair of horizontal coils located, in a plane substantially parallel to said surface of tissue.

6. The neuromagnetic apparatus of claim 1 wherein said control circuit further comprises means for adjusting a ratio of current in each coil of said at least one pair of adjacent eccentric coils to vary a position of said peak electric field focus.

7. The neuromagnetic apparatus of claim 1 wherein said control circuit further comprises means for adjusting a magnitude of current in said at least one pair of adjacent eccentric coils to vary a depth of said peak electric field focus.

8. The neuromagnetic apparatus of claim 1 wherein said at least one pair of adjacent eccentric coils comprise two pairs of adjacent eccentric coils wherein said control circuit adjusts current in each of said pair for steering a location of said peak electric field focus in said tissue, one of said pair being superimposed over the other of said pair at a predetermined rotation angle.

9. The neuromagnetic apparatus of claim 8 wherein said predetermined rotation angle is about 90 degrees.

10. The neuromagnetic apparatus of claim 1 wherein said control circuit comprises:
at least one charge unit connected across each coil of said at least one pair of adjacent eccentric coils,
a plurality of switches, each switch in series with said each coil, and connected to an output of said at least one charge unit,
a controller interconnected between said at least one charge unit and said switches, said controller activating said switches to apply current from said at least one charge unit to said at least one coil synchronously and in phase.

11. The neuromagnetic apparatus of claim 1 wherein said control circuit comprises:
at least one SQUID detector connected across each coil of said at least one pair of adjacent eccentric coils,
an amplifier connected to the output of each SQUID detector,
a weighting scanner connected to the outputs of said amplifiers,
a signal processor connected to an output of said weighting scanner, and
a controller connected to said weighting scanner and to said signal processor.

12. The neuromagnetic apparatus of claim 1 wherein each coil in said at least one pair of adjacent eccentric coils comprises:
a. a coil diameter ranging from about 1 to 10 cm,
b. a number of turns ranging from about 1 to 10 turns, and
c. a cross-sectional area ranging from about 1 to 10 mm$^2$.

13. A neuromagnetic method for providing a peak electric field focus in a target region of subcutaneous nerve tissue beneath a surface of tissue, said method comprising the steps of:

orienting first and second eccentric coils adjacently near said surface of tissue, each one of said first and second eccentric coils having a broad first low-field region produced near said surface of tissue, and a second narrow high-field region produced below said surface of tissue and said first and second coils connected to a control circuit by separate electrical paths;

adjusting or sensing a first current in said eccentric first coil in a first direction, said first current corresponding to a first electric field in said subcutaneous nerve tissue;

adjusting or sensing a second current in the second eccentric coil in a second direction, said second direction being electrically separate and opposite to said first direction in said region of adjacency of said first and second coils, said second current corresponding to a second electric field in said subcutaneous nerve tissue, synchronously-simultaneously operating said first and second coils, generating or sensing an electric field peak focus in said target region in said subcutaneous nerve tissue through said synchronous-simultaneous interaction of said first electric field and said second electric field.

14. The neuromagnetic method of claim 13 wherein said orienting step occurs with said first coil oriented substantially parallel to and above said surface of tissue and with said second coil substantially orthogonal to said surface of tissue.

15. The neuromagnetic method of claim 13 further comprising the step of:
adjusting a ratio of current in said first coil with respect to current in said second coil to position said peak electric field focus in said subcutaneous nerve tissue.

16. The neuromagnetic method of claim 13 further comprising the step of:
adjusting a magnitude of current in said first coil and current in said second coil to control a depth of said peak electric field focus in said subcutaneous nerve tissue.

17. The neuromagnetic method of claim 13 further comprising the step of:
providing current to said first and second coils to produce a maximum electric field in said target region and a minimum electric field between said surface of tissue and said target region so as to stimulate said subcutaneous nerve tissue in said target region.

18. The neuromagnetic method of claim 13 further comprising the steps of:
sensing current in said first and second coils to detect nerve currents in said subcutaneous nerve tissue in said target region; and
weighting said sensed current from said sensing step such that a desired depth of focusing is produced and a reduction of fields in a region of adjacency of said first and second coils is obtained.

* * * * *